(12) United States Patent
West

(10) Patent No.: US 10,761,345 B2
(45) Date of Patent: Sep. 1, 2020

(54) MOTION SICKNESS PREVENTION EYEWEAR

(71) Applicant: Jerry Wayne West, Dale, TX (US)

(72) Inventor: Jerry Wayne West, Dale, TX (US)

( * ) Notice: Subject to any disclaimer, the term of this patent is extended or adjusted under 35 U.S.C. 154(b) by 171 days.

(21) Appl. No.: 16/129,245

(22) Filed: Sep. 12, 2018

(65) Prior Publication Data

US 2019/0079314 A1 Mar. 14, 2019

Related U.S. Application Data

(60) Provisional application No. 62/557,567, filed on Sep. 12, 2017.

(51) Int. Cl.
*G02C 5/00* (2006.01)
*A61M 21/02* (2006.01)
*G02C 7/00* (2006.01)
*G02C 7/10* (2006.01)
*A61F 9/04* (2006.01)

(52) U.S. Cl.
CPC ............. *G02C 5/001* (2013.01); *A61M 21/02* (2013.01); *G02C 5/008* (2013.01); *G02C 7/00* (2013.01); *G02C 7/105* (2013.01); *A61F 9/045* (2013.01)

(58) Field of Classification Search
CPC .......... G02C 5/001; G02C 7/105; G02C 7/00; G02C 5/008; A61M 21/02; A61F 9/045
USPC .................................................... 351/41, 158
See application file for complete search history.

(56) References Cited

U.S. PATENT DOCUMENTS 9,977,262 B2 * 5/2018 Boulton ................. G02C 7/101

* cited by examiner

*Primary Examiner* — Tuyen Tra
(74) *Attorney, Agent, or Firm* — Dunlap Bennett & Ludwig, PLLC; Brendan E. Squire

(57) ABSTRACT

A motion sickness prevention eyewear presents a demarcation line in a field of view in a lens assembly. The demarcation line varies relative to the orientation of the eyewear to present a visual depiction corresponding to a natural horizon. The eyewear includes at least lens assembly that has an interior cavity defined between an inner lens, an outer lens, and a sidewall defined to join the lenses around the periphery of the lens assembly. A volume of liquid is carried in the interior cavity. The volume if liquid is responsive to changes in the orientation of the eyewear relative to the horizon.

12 Claims, 3 Drawing Sheets

MOTION SICKNESS PREVENTION EYEWEAR

CROSS-REFERENCE TO RELATED APPLICATION

This application claims the benefit of priority of U.S. provisional application No. 62/557,567, filed Sep. 12, 2017, the contents of which are herein incorporated by reference.

BACKGROUND OF THE INVENTION

The present invention relates to motion sickness, and more particularly to eyewear for reducing the incidence of motion sickness.

Motion sickness can be debilitating to travelers in land vehicles, water vessels, and aircraft. Often, motion sickness can be triggered by the victim losing a visual reference for the horizon while the craft they are traveling in is moving.

Other devices require technically difficult implementations to try to provide a visual reference for the horizon. These other devices, typically an attitude indicator, are generally incorporated in the control station of the craft for use by a crewmember responsible for operation of the craft, rather than for occupants of the craft. Accordingly, these systems would be expensive and difficult to provide for individual use.

As can be seen, there is a need for an apparatus and method for reducing the incidence of motion sickness for a traveling occupant of a craft.

SUMMARY OF THE INVENTION

In one aspect of the present invention a motion sickness prevention eyewear is disclosed. The eyewear includes a frame adapted to be worn on the head of a user. At least one lens assembly is mounted in the frame. The at least one lens assembly has an inner lens and an outer lens disposed in a spaced apart relation by at least one sidewall to define an interior cavity within the lens assembly. A volume of a liquid is provided within the interior cavity to fill a lower portion of a field of view through the lens to present a demarcation line that varies with the orientation of the eyewear to correspond to a natural horizon line.

The liquid may have a selected tint. The selected tint may corresponds to a predetermined environmental use of the eyewear. In other embodiments, a colorant provides the selected tint.

In some embodiments, the at least one lens assembly includes a first lens assembly and a second lens assembly.

The sidewall may be formed of a bonding agent. The bonding agent may be resiliently sealable when penetrated by an injection needle.

A remaining volume of the interior cavity may include an immiscible fluid. In other embodiments, a remaining volume may be a vacuum applied to the interior cavity.

In some embodiments the frame is an eyeglass frame. In other embodiments, the frame may be a goggle structure.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, embodiments of the present invention provide an apparatus and method for reducing the incidence of motion sickness. Embodiments of the invention provide an eyewear that presents a visual depiction of the horizon in the wearer's field of view.

Figure 1:
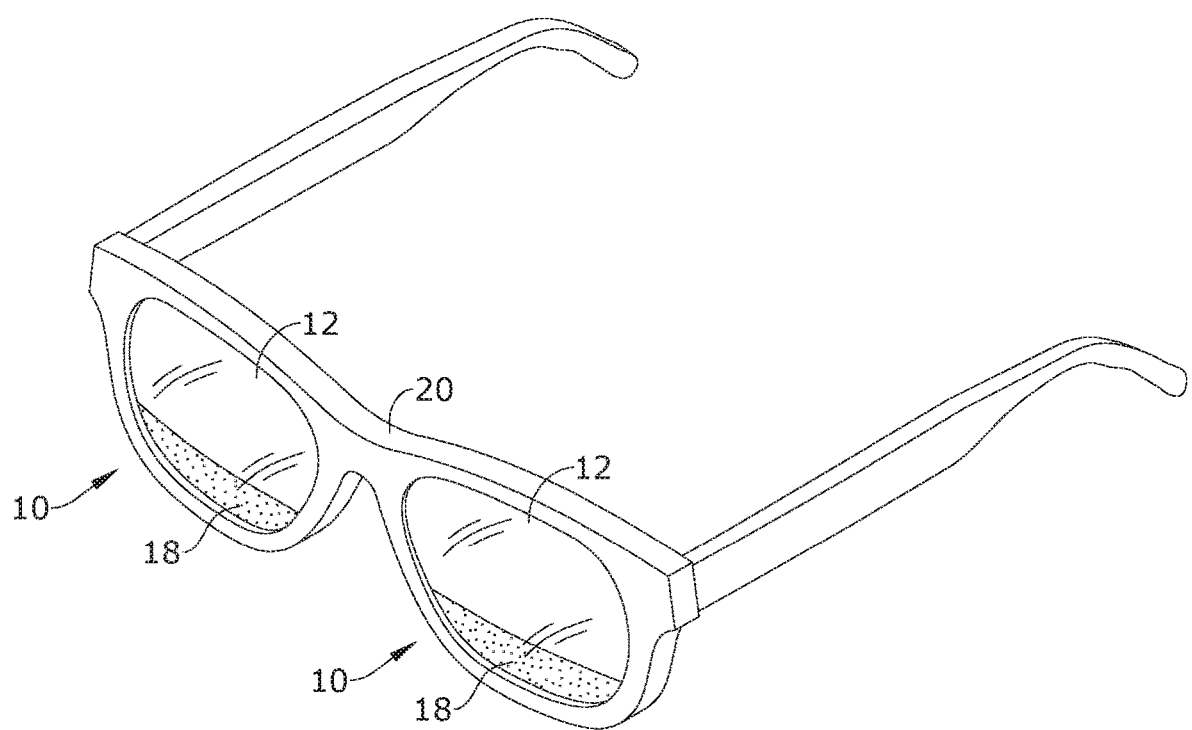
FIG. 1 is a perspective view of the motion sickness prevention eyewear, shown in an exemplary installation.
Figure 2:
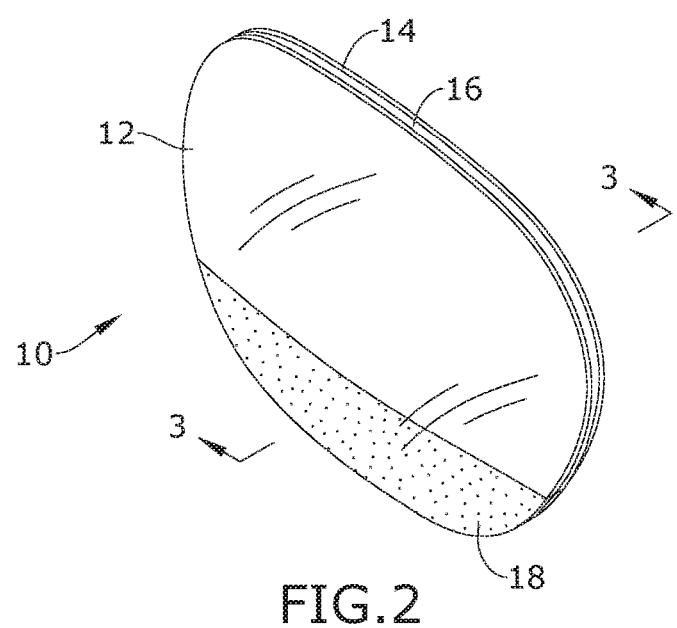
FIG. 2 is a perspective view of a single lens assembly 10.
Figure 3:
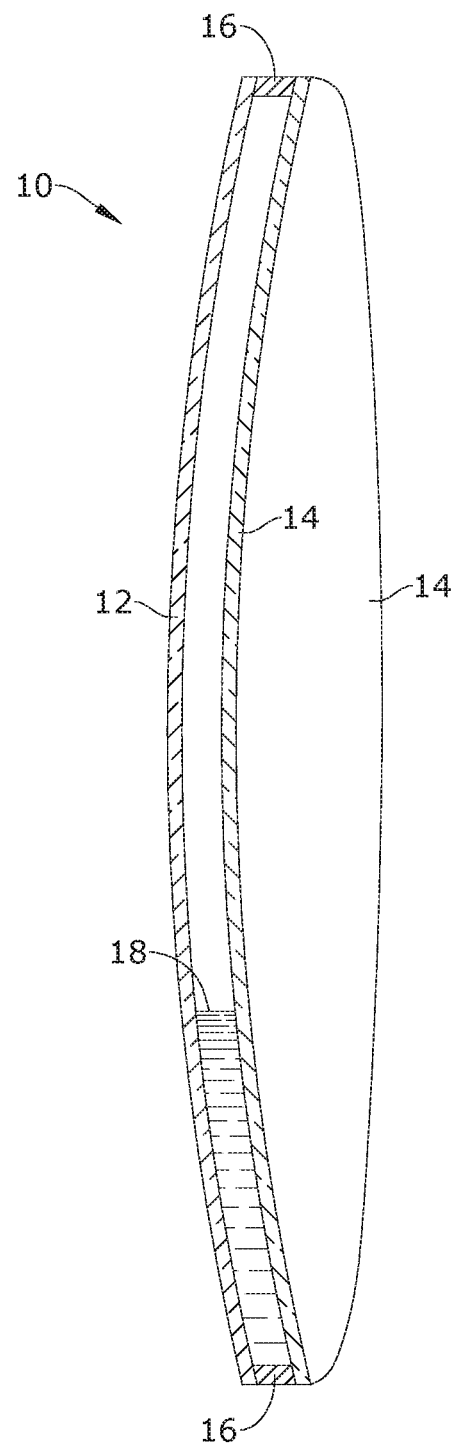
FIG. 3 is a section view of the invention, taken along line 3-3 in FIG. 2.

As seen in reference to FIGS. 1-3, a non-limiting embodiment of the motion sickness prevention eyewear is illustrated. The motion sickness prevention eyewear includes at least one lens assembly 10 that is mounted in an eyewear frame 20. In other embodiments, the eyewear may have binocular lenses mounted in the eyewear frame. While depicted as a conventional eyeglass frame, the eyewear frame 20 may alternatively include a goggle type configuration, which may or may not restrict visibility in the peripheral areas in the user's field of view.

The lens assembly 10 includes an outer lens 12 and an inner lens 14 that are disposed in a spaced apart relation with an outer sidewall 16 joining the outer lens and the inner lens 14 to define an interior cavity. The lenses 12, 14 may be corrective lenses to accommodate the visual acuity of the wearer or non-corrective for wearers who do not require corrective glasses, or who may be wearing contact lenses.

The sidewall 16 may be formed of a like material as that of the lenses 12, 14. Alternatively, the sidewall 16 may be formed of an adhesive or a bonding agent. Preferably the sidewall 16 is formed of a resilient material, through which an injection needle can be inserted to inject a volume of liquid into the interior cavity.

The interior cavity is partially filled with a volume of liquid 18. The volume of liquid 18 is such that a demarcation line 24 is provided between the liquid 18 and the remainder of the interior cavity. The demarcation line 24 is presented in the visual field of the wearer when the eyewear is worn by the user. The demarcation line 24 varies with the orientation of the eyewear to present a visual depiction to correspond to a horizon line 22.

While focal properties of the liquid 18 may provide a suitable visual demarcation line 24 for the wearer, the liquid 18 may be tinted in its natural state, or may be tinted with a colorant to provide a more distinguishable demarcation line 24. The liquid 18 should be slightly viscous to permit non-turbulent movement of the liquid 18 within the interior cavity so that is responsive to movements.

The remaining volume may be occupied with a fluid that is immiscible with the liquid 18. In other embodiments, a vacuum may be applied to the interior cavity so that the remaining volume is substantially evacuated. The colorant may be selected to correspond to the environment in which the eyewear may be worn. By way of non-limiting example, the colorant may have a bluish tint to correspond to eyewear intended for watercraft.

Figure 4A:
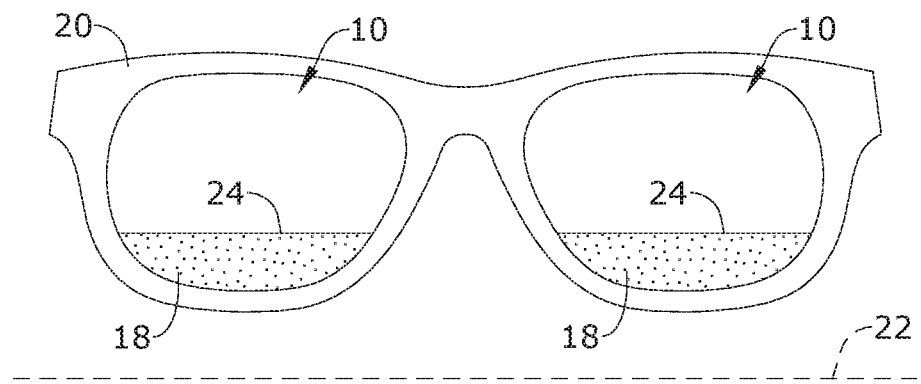
FIG. 4A is a front schematic view of the invention, showing the alignment of the true and artificial horizons when level.
Figure 4B:
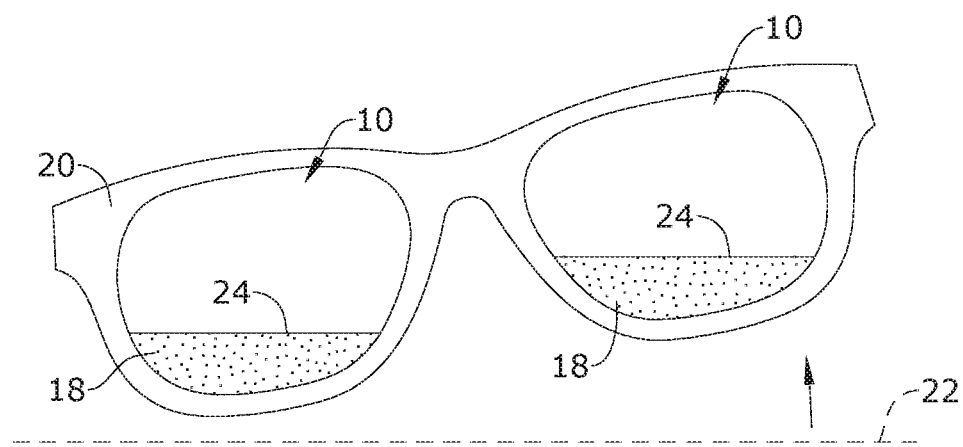
FIG. 4B is a front schematic view of the invention, showing the maintained artificial horizon when tiled.
Figure 4C:
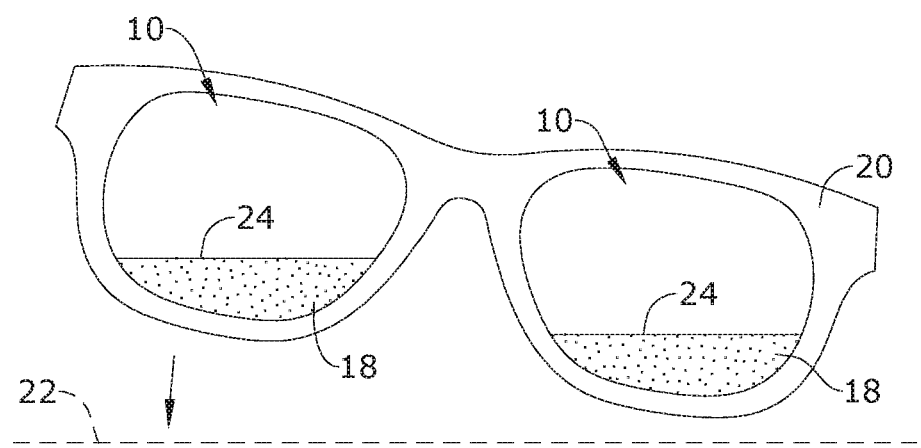
FIG. 4C is a front schematic view of the invention, showing the maintained artificial horizon when tiled.

As seen in reference to FIGS. 4A-4C, the operation of the motion sickness prevention eyewear is demonstrated in use. In FIG. 4A, the eyewear is shown in a level attitude in which the demarcation line 24 is parallel to a horizon line 22. In FIG. 4B, the eyewear is demonstrated where the wearer is tilted to the right relative to the horizon 22. As seen in the drawing, the volume of liquid 18 moves within the interior cavity such that the demarcation line 24 is presented to correspond to the horizon 22. In FIG. 4C, the eyewear is shown in a tilt to the left. In this case, the liquid 18 moves within the interior cavity relative to the horizon 22 such that the demarcation line 24 presents a visual depiction of the horizon line 22.

It should be understood, of course, that the foregoing relates to exemplary embodiments of the invention and that modifications may be made without departing from the spirit and scope of the invention as set forth in the following claims.

What is claimed is:

1. A motion sickness prevention eyewear, comprising:
   a frame adapted to be worn on the head of a user;
   at least one lens assembly mounted in the frame, the lens assembly having an inner lens and an outer lens disposed in a spaced apart relation by at least one sidewall defining an interior cavity within the lens assembly; and
   a volume of a liquid within the interior cavity to fill a lower portion of a field of view through the lens to present a demarcation line that varies with the orientation of the eyewear to correspond to a natural horizon line.

2. The motion sickness prevention eyewear of claim 1, wherein the liquid has a selected tint.

3. The motion sickness prevention eyewear of claim 2, wherein the selected tint corresponds to a predetermined environmental use.

4. The motion sickness prevention eyewear of claim 2, wherein a colorant provides the selected tint.

5. The motion sickness prevention eyewear of claim 1, wherein the at least one lens assembly includes a first lens assembly and a second lens assembly.

6. The motion sickness prevention eyewear of claim 1, wherein the sidewall is formed of a bonding agent.

7. The motion sickness prevention eyewear of claim 6, wherein the bonding agent is resiliently sealable when penetrated by an injection needle.

8. The motion sickness prevention eyewear of claim 1, wherein a remaining volume of the interior cavity includes an inert gas.

9. The motion sickness prevention eyewear of claim 1, wherein a vacuum is applied to the interior cavity.

10. The motion sickness prevention eyewear of claim 1, wherein the frame is an eyeglass frame.

11. The motion sickness prevention eyewear of claim 1, wherein the frame is a goggle.

12. A motion sickness prevention eyewear, comprising:
    at least one lens assembly, the lens assembly having an inner lens and an outer lens disposed in a spaced apart relation by at least one sidewall defining an interior cavity within the lens assembly; and
    a volume of a liquid within the interior cavity to fill a lower portion of a field of view through the lens to present a demarcation line that varies with the orientation of the eyewear to correspond to a natural horizon line.

* * * * *